(12) United States Patent
Oberhoff et al.

(10) Patent No.: US 7,586,813 B2
(45) Date of Patent: Sep. 8, 2009

(54) SIGNAL PROCESSING APPARATUS FOR AN ULTRASOUND TRANSDUCER, ULTRASOUND RECEIVER AND METHOD FOR OPERATING AN ULTRASOUND RECEIVER

(75) Inventors: Dietmar Oberhoff, Leichlingen (DE); Guido Flohr, Hürth (DE); Günther Coen, Velbert (DE)

(73) Assignee: Betriebsforschunginstitut VDEH-Institut für Angewandte Forschung GmbH, Düsseldorf (DE)

( * ) Notice: Subject to any disclaimer, the term of this patent is extended or adjusted under 35 U.S.C. 154(b) by 532 days.

(21) Appl. No.: 11/189,110

(22) Filed: Jul. 25, 2005

(65) Prior Publication Data

US 2006/0036171 A1 Feb. 16, 2006

(30) Foreign Application Priority Data

Jul. 23, 2004 (DE) .................. 10 2004 035 950

(51) Int. Cl.
*A61B 8/00* (2006.01)
(52) U.S. Cl. .................................................. 367/135
(58) Field of Classification Search ............... 367/135, 367/178; 600/437; 341/155
See application file for complete search history.

(56) References Cited

U.S. PATENT DOCUMENTS

| 4,090,145 A | | 5/1978 | Webb | |
|---|---|---|---|---|
| 5,005,419 A | * | 4/1991 | O'Donnell et al. | 600/447 |
| 5,482,044 A | * | 1/1996 | Lin et al. | 600/443 |
| 5,987,966 A | | 11/1999 | Fontanille et al. | |
| 6,033,225 A | | 3/2000 | Pike | |
| 6,530,890 B2 | * | 3/2003 | Bang et al. | 600/454 |
| 6,590,517 B1 | * | 7/2003 | Swanson | 341/155 |
| 2002/0060751 A1 | | 5/2002 | Rowe et al. | |
| 2002/0121142 A1 | * | 9/2002 | Bae et al. | 73/602 |
| 2002/0176577 A1 | | 11/2002 | Xu | |
| 2003/0028103 A1 | | 2/2003 | Miller | |
| 2004/0081340 A1 | * | 4/2004 | Hashimoto | 382/128 |
| 2005/0251035 A1 | * | 11/2005 | Wong et al. | 600/437 |
| 2006/0036171 A1 | * | 2/2006 | Oberhoff et al. | 600/437 |

FOREIGN PATENT DOCUMENTS

| EP | 1 416 443 A1 | 5/2004 |
|---|---|---|
| JP | 62153756 A | 7/1987 |
| WO | WO99/23760 A | 11/1998 |

OTHER PUBLICATIONS

"Halbleiter-Schaltungstechnik" (*Semiconductor Control Technology*) by U. Tietze and Ch. Schenk, Springer Verlag, Heidelberg, 2002, 12$^{th}$ ed., at p. 1031, et seq., U. Tietze and Ch. Schenk, p. 1308, et seq.
R. Fink et al.: "Empfangskonzept für einen digitalen Empfänger", in: NTZ Archiv, vol. 5, No. 12, 1983, pp. 353-358.

* cited by examiner

*Primary Examiner*—Dan Pihulic
(74) *Attorney, Agent, or Firm*—Henry M. Feiereisen; Ursula B. Day

(57) ABSTRACT

To reduce signal interference and improve the signal-to-noise ratio in the transmitted signal, the analog signals produced by an ultrasound transducer are promptly digitized. In accordance with the invention, the demodulator is already shielded from the ultrasound transducers, immediately after the preamplifier, which is itself shielded from the ultrasound transducers, by an analog to digital converter, for example.

30 Claims, 2 Drawing Sheets

SIGNAL PROCESSING APPARATUS FOR AN ULTRASOUND TRANSDUCER, ULTRASOUND RECEIVER AND METHOD FOR OPERATING AN ULTRASOUND RECEIVER

CROSS-REFERENCES TO RELATED APPLICATIONS

This application claims the priority of German Patent Application, Serial No. 10 2004 035 950.4, filed Jul. 23, 2004, pursuant to 35 U.S.C. 119(a)-(d), the subject matter of which is/are incorporated herein by reference.

BACKGROUND OF THE INVENTION

The present invention pertains to a signal processing apparatus for ultrasound transducers, and to an ultrasound receiver apparatus. More particularly, the present invention directed to improving the signal received by such apparatus.

Ultrasound receiver may be used, for example, for non-destructive materials testing of tubes, wires or belts, by generating an ultrasound wave in the test object, e.g. by means of a piezo-electric test head or, for non-contact applications, by means of an electromagnetic acoustic transducer (EMAT). The emitted ultrasound signal is then picked up by the ultrasound receiver and converted into an output signal. Information about flaws in the material of the test object is detected in the pattern of the output signal. However, for EMATs, the problem from the beginning has been that the amplitude of the ultrasound signal produced is very small, because an EMAT has about 10% of the effectiveness of a piezoelectric transducer. The remedy has been to use costly, more powerful transmitters.

In particular, the ultrasound receivers used for non-destructive testing are beset by serious environmental signal distortion problems. Strong interference signals caused by the drives of the rolling frame in a rolling mill are generated during testing the material. These interference signals interfere also with the ultrasound signal, and with the processing of the ultrasound signal into an output signal. Such interference effects reduce the interpretability of the detection signal. In some instances, this makes meaningful analysis of the signal impossible.

In the past, attempts were made to shield the analog electric equipment following the ultrasound transducers against such interference. However, such shields are costly. Moreover, the installation space is limited in immediate proximity to the ultrasound transducer in many areas of their application. For that reason, the ultrasound transducer is typically separated from the subsequent analog electrical detection circuits. As a result of these inalterable spatial circumstances, it was necessary to date to connect the ultrasound transducer to the electronic evaluation assembly by a cable of a length of up to 30 m. Still these cables, as well as the electronic evaluation assembly, are exposed to strong interference signals in their working environment so that it has not been possible to date to generate signals having a large separation between the signal- and interference and a large signal-to-noise ratio.

It would therefore be desirable and advantageous to provide an improved ultrasound receiver to obviate prior art shortcomings and to exhibit great signal-to-noise ratio and great wanted-to-unwanted signal ratio.

SUMMARY OF THE INVENTION

According to one aspect of the present invention, a signal processing apparatus for an ultrasound transducer, includes a first preamplifier for amplifying an analog signal produced by an ultrasound transducer to generate an amplified analog signal, and a first analog-to-digital converter directly connected to the preamplifier for producing a first digital signal from the amplified analog signal The present invention resolves prior art problems by realizing a prompt digitalization of the analog signal produced by the ultrasound transducer. In accordance with the invention, the digitalization is achieved already between the ultrasound transducer and the demodulator, suitably through an analog-to-digital converter, which is directly connected to a preamplifier connected to the ultrasound transducer.

As a result of the prompt digitalization of the analog signal produced by the ultrasound transducer, the further signal processing performed by the ultrasound receiver produces a digital output signal that is less susceptible to interference signals. Furthermore, prompt digitalization permits an increase of the useful signal range. While conventional systems generate signals of about 65 dB dynamic range, it is possible for systems in accordance with the present invention to use signals having a 120 dB (signal dynamic 1,000,000/1) dynamic range. The signal's dynamic range can be increased even further in the future by speeding up the clock frequency and improving the response of digital components in the electronic evaluation assembly. The dynamic range made possible by the invention allows a simplification of the system by the absence of a controllable preamplifier and the use of only a constant preamplifier, because only rough adjustment of the analog signal produced by the ultrasound transducer to the dynamic range of the analog-to-digital converter is sufficient. All the rest of the signal processing is digital. The use of a constant preamplifier allows also simplification or elimination of interference-prone components, in particular analog components, so that signal disturbances can be reduced even prior to the analog-to-digital converter.

The predominantly digital configuration of signal processing permits signal processing to be carried out with only a single power pack. The use of a single power pack is easy to shield without incurring high costs. Conventional analog signal processing units required various power packs to supply energy to the various components. As a consequence, the number of areas where interference can be introduced into the system increased, and the shielding for the numerous power packs incurred high costs so that oftentimes the power packs were not sufficiently shielded.

The benefits of the invention are mainly realized by the configuration of the signal processing apparatus and primarily independent of the type of ultrasound transducer used. For reasons of completeness, the invention will however mainly be described with reference to an ultrasound receiver that comprises an ultrasound transducer and the signal processing apparatus according to the configuration of the invention, not limiting the disclosure of the invention to such ultrasound receivers, however.

According to another feature of the present invention, the ultrasound transducer may be implemented as an electromagnetic acoustic transducer (EMAT). Of course, the use of a piezo-electric transducer or other suitable transducer may also be conceivable instead.

According to another feature of the present invention, the analog-to-digital converter has at least a 14-bit resolution and at least a 50 MHz clock frequency, preferably an 80 MHz clock frequency. Selection of an output and clock frequency requires an optimal compromise between equipment cost, which increases as the resolution increases, and the resolution. Increasing the resolution by one bit doubles the resolution of the converter, whereas a doubling of the clock frequency merely realizes an enhancement of $\sqrt{2}$. An increase of the resolution allows production of precise signals, even when the clock-frequency is lower, compared, for example, to an analog-to-digital converter having a resolution of 8 bit and a clock frequency of 500 Mhz, even though such analog-to-digital converters may certainly also be used in an ultrasound receiver according to the present invention.

According to another feature of the present invention, the digital demodulator executes a Hilbert transform. An example of this type of demodulation is described, i.a., in the publication *Discrete-time Signal Processing* 2nd edition, by A. V. Oppenheim and R. W. Schafer, Prentice-Hall, N.J., 1999. Hilbert transforms are sometimes also referred to as quadrature modulators.

A Hilbert transform, or a transform very similar to a Hilbert transform is realized, when the demodulator has a so-called "quadrature numerically-controlled oscillator" (NCO), an I/Q mixer, a "cascaded-integrator comb" (CIC) filter, a "finite impulse-response" (FIR) filter, and a cartesian-to-polar converter. An explanation of FIR filters is available in the publication Halbleiter-Schaltungstechnik (*Semiconductor Control Technology*) by Tieze and Schenk, Springer Verlag, Heidelberg, 2002, 12$^{th}$ ed., at page 1031, et seq. I/Q mixers, as used as a preferred part of the demodulator, are described by Tieze and Schrank at page 1308, et seq.

According to another feature of the present invention, the ultrasound receiver may include a median-filter. The median-filter may hereby be constructed in such a manner as to produce an output signal which is determined by median filtering a sequence of digital signals.

In non-destructive material testing, a time-graded sequence of signals is sent out by the ultrasound transmitter. For example, 100 to 150 signals per second may be emitted. The ultrasound receiver takes those signals that come to it within a given time window, and converts them into an electric signal. As window, oftentimes the region is selected which is passed by the ultrasound wave propagating directly from the transmitter to the receiver through the test object up to a fixed time-limited cut-off. The signals produced by the ultrasound transducer thus reflects the passage of the ultrasound wave propagating immediately from the ultrasound transducer to the receiver through the test object, and the—later—passage of likely reflections of portions of the originally-transmitted ultrasound wave that spreads out in other directions. With respect to the median filtering, the next signal in the filtered sequence of signals is considered as the portion of the electric signal, produced by the ultrasound transducer, that appears in the window beginning, for example, with the passage of the next ultrasound wave which propagates directly from the transmitter to the receiver through the test object. The windows are defined in such a way as to have a comparable starting point in time, for example when the respective ultrasound signal is sent out.

In testing metal bands, examining an area of a width of 2 m, a 400 μs window can be used and the next signal is sent after about 6 milliseconds. The response signal produced by the 400 μs window is transferred during signal processing to a row of 32,000 sampling points.

Following demodulation, each signal is comprised of a row of values in which each subsequent value in the row represents the value of the signal at the next sampling point. The row has "in" values, wherein "in" is the number of samples recorded during the sampling window for generating an output signal.

According to another feature of the present invention, the median filter may transfer the row of sampling values for a digitalized signal to a column in an input matrix. Another column is provided for the row of sampling values produced by the next signal. By providing similar beginning points for the sampling windows used for generating the output signal and the same sampling, corresponding samples are placed in the same locations in their respective columns in comparison to the time point at which the sampling window opens.

The median filter provides "n" columns in an input matrix, such that "n" is the number of signals that the median filter evaluates, so that the result array of the median filter also provides places for "n" result values. For example "n" can be any uneven number, in particular: 3, 5, or 1. In filtering, the median filter reads out the row of values for one of the sampling times from the "n" columns in the input matrix, sorts these values according to size, and outputs the value in the middle, that is, the "median" value. If n=3 then the median value is the value in the second place in the sorted set of values; if n=5, the third place, and so on. This middle value is then written into a results array which either provides the output signal, or can be processed to provide the output signal. The median filter filters out stochastic interference which is asynchronous with the return frequency.

The ultrasound transducer may include a switched bypass for the median filter so that the signals can be processed without using the median filter. For example, this permits the action and effectiveness of the median filter to be analyzed.

According to another feature of the present invention, the ultrasound receiver may have a connection to a computer network, such as an internet. Suitably, the connection may be an Ethernet connection, preferably one using the TCP/IP protocol. Optical data transmission can be provided within the computer network, whereby the computer system is galvanically isolated from the ultrasound system, and signal interference is further reduced.

According to another feature of the present invention, the ultrasound receiver may be constructed to produce ultrasound signals which pass the ultrasound transducer in a same direction. This unidirectional testing prevents the ultrasound receiver from picking up erroneous signals, such as echo returns, in the opposite direction.

According to another feature of the present invention, the ultrasound receiver may have a first ultrasound transducer producing a first analog signal that is amplified by a first preamplifier, and an analog-to-digital converter which is directly connected to the preamplifier for producing a digital signal from the amplified analog signal. A second ultrasound transducer produces a second analog signal that is then amplified by a second preamplifier, and a second analog-to-digital converter that is connected directly the preamplifier for producing a second digital signal from the second amplified analog signal. Also, the ultrasound receiver may be constructed with a first ultrasound transducer for producing a first analog signal, a first analog-to-digital converter for producing a first digital signal from the first analog signal, a second ultrasound transducer for producing a second analog signal, and a second analog-to-digital converter for producing a second digital signal from the second analog signal, and a demodulator for producing a demodulated digital signal.

The ultrasound transducers may be arranged in spatially offset relationship, especially at a distance from each other that is at a quarter of the wavelength (λ/4) of the returned ultrasound signal that is picked up by the transducers. Advantageously, the first and second preamplifiers are constructed together as a single component. Suitably, the preamplifiers may be constructed as differential amplifier.

The embodiments described above provide a send/return separation of 25 dB and, in some cases, 40 dB.

In the embodiments described above, the unidirectionality is realized in particular by a multiplier for the first digital signal, a delay element for the second digital signal, and an adder for adding the digital output signal of the multiplier and the digital output signal of the delay element. The delay element unit can shorten the second digital signal by the time which corresponds to the distance of the second ultrasound transducer from the first ultrasound transducer at the frequency of the received ultrasound signal. Depending on the signal propagation direction, the signals, received in staggered sequence, are added constructively or, if they come from the opposite direction, added destructively, so that the signals substantially cancel out in a propagation direction.

According to another feature of the present invention, the multiplier may be configured with adjustable multiplication factor, and/or may include a delay element with adjustable delay. An analyzer for monitoring the first and second digital signal may determine the multiplication factor and/or the delay to be adjusted. By adjusting the multiplication factor or the delay element, a lack of precision resulting from manufacturing variations in the construction of the ultrasound transducer can be compensated, for example in the separation of the two ultrasound transducers from the surface of the tested material, or in the pickup sensitivity of the respective ultrasound transducer. In particular, the analyzer can determine the delay being adjusted based on the relative position of the zero passages of the first and second digital signals with respect to each other. Normally, the delay is t/4, when the ultrasound transmitters are offset by a quarter wavelength ($\lambda/4$).

According to another aspect of the present invention, a signal processing apparatus for an ultrasound transducer, includes a first analog-to-digital converter producing a first digital signal from an analog signal produced by an ultrasound transducer and a demodulator producing a first demodulated digital signal from the digital signal produced by the analog-to-digital converter According to yet another aspect of the present invention, an ultrasound receiver includes an ultrasound transducer adapted to produce an analog signal, a preamplifier for amplifying the analog signal to provide an amplified analog signal, and an analog-to-digital converter directly connected to the preamplifier for producing a digital signal from the amplified analog signal.

An ultrasound receiver, as described above, can also be used as a receiver for receiving other AM-modulated signals. In particular, an ultrasound receiver in accordance with the invention can be used as receiver for receiving radar or radio signals, whereby a transducer is used instead of an ultrasound transducer so that radar or radio signals are used, instead of ultrasound signals.

An ultrasound receiver is especially applicable for non-destructive material testing, and especially for the non-destructive testing of metals (bands, tubes and wires) during manufacture or further shaping operations of these materials. Machinery is hereby used which generate strong interference signals, so that conventional ultrasound receivers could not reliably provide a great signal-to-noise ratio and an optimal wanted-to-unwanted signal ratio.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
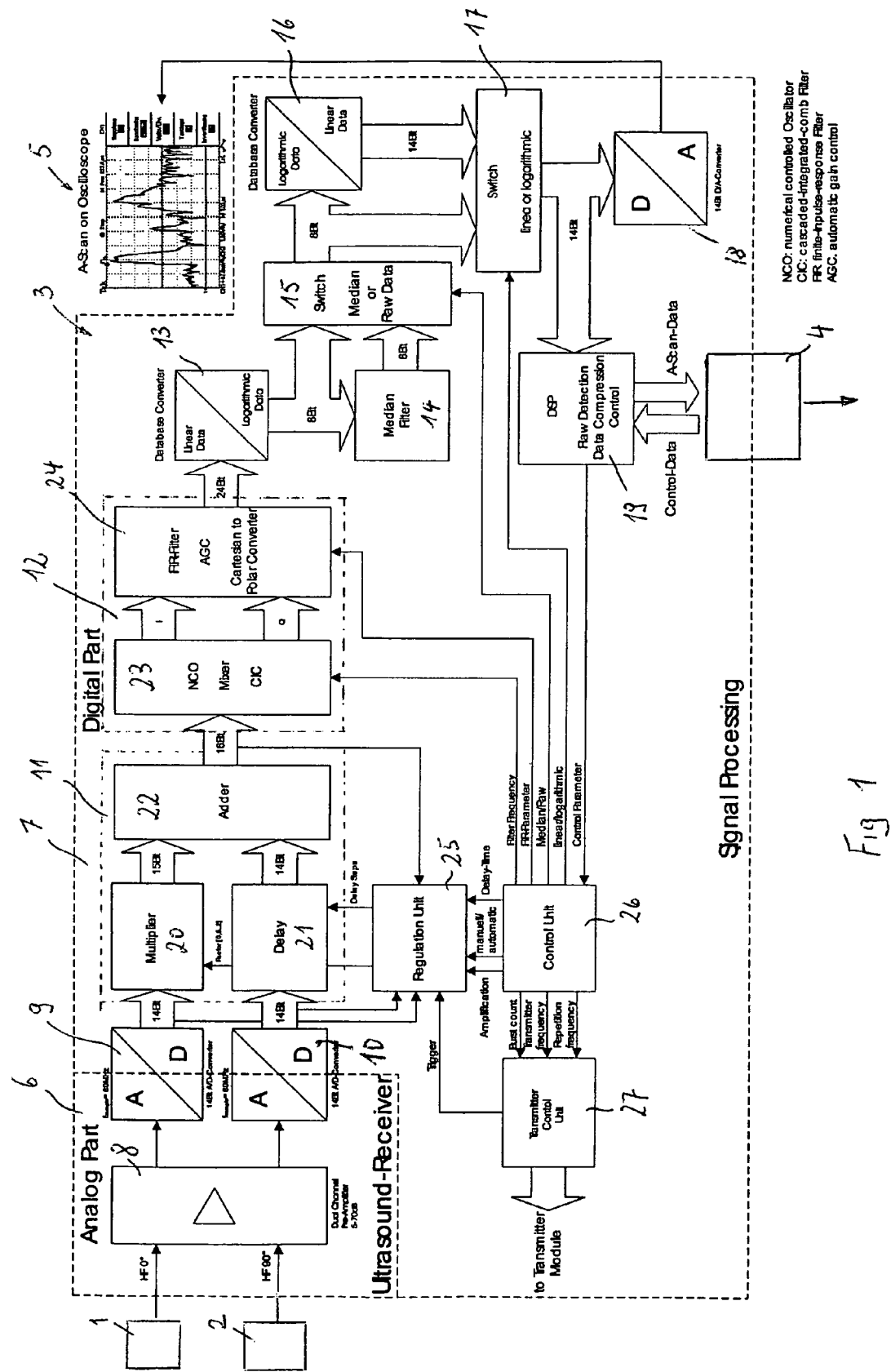
FIG. 1 is a block diagram of a signal receiver in accordance with the present invention.

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a block diagram of a signal receiver in accordance with the present invention, depicting an ultrasound receiver having two ultrasound transducers 1, 2, and a signal processing unit 3 connected to the ultrasound transducers 1, 2. The output of the signal processing apparatus 3 is an Ethernet connection 4 and a display 5 in the form of an oscilloscope trace 5.

The ultrasound transducer is preferably designed as an EMAT. The coil of the EMAT of the first ultrasound receiver 1 is offset at a quarter-wavelength distance ($\lambda/4$) from the coil of the EMAT of the second ultrasound receiver 2. The first ultrasound receiver 1 generates a first analog signal HF0° which leads the analog signal HF90° produced by the second ultrasound receiver 2 by a phase shift of $\lambda/4$.

The signal processing unit 3 has an analog portion 6 and a digital portion 7. Even though these separate elements 6, 7, of the signal processor 3 are shown in close proximity of each other in FIG. 1, they can (also within a given component), of course, be arranged so as to be spatially separated from each other, if available spatial conditions so dictate.

The analog portion 6 of the signal processing unit 3 has a preamplifier 8. The preamplifier 8 is designed as a so-called "dual-channel" preamplifier, and provides 5 to 70 dB of amplification. The preamplifier 8 outputs the first analog signal HF0° as an amplified analog signal. At the same time, the preamplifier 8 outputs the second analog signal HF90° as a second amplified analog signal. The first and second amplified analog signals are supplied to respective analog-to-digital converters 9, 10, and converted there into first and second digital signals, respectively. The analog-to-digital converters 9, 10 have a clock frequency of 80 MHz and a resolution of 14-bit. Thus, the first and second digital signals are 14-bit signals.

The first and second digital signals are fed to a directional evaluation apparatus 11 which generates a digital signal which assumes values other than zero only when the ultrasound wave passes the ultrasound transducer in a predetermined direction. For each ultrasound wave that passes the ultrasound transducers 1, 2, in opposite direction, this digital signal outputted by the directional evaluation apparatus 11 assumes a zero value. The generated digital signal is a 16-bit signal.

The digital signal thus generated by the directional evaluation apparatus 11 is then supplied to a down-converter 12 where it is demodulated from signal with 16 bit and 80 Mhz to a signal of 24-bit and 1 MHz. This filters the 16-bit signal from the carrier frequency, leaving only the useful signal that contains the test result information. A converter 13 is connected to the down converter 12 to change linear data to logarithmic data, by using tables, for example. The thus-generated 8-bit signal is supplied to a median-filter 14 and a switch 15. The signal output by the median-filter 14 is supplied to the switch 15 as well. The output signal of the switch 15 is supplied to a converter 16 which changes logarithmic data to linear data. Output signals from the switch 15 and the converter 16 are supplied to a further switch 17. The signal output by the switch 17 is supplied to a digital-to-analog converter 18 that can provide an analog signal to the display 5. Furthermore, the output signal of the switch 17 is further supplied to a data processing module 19 which can execute a preliminary analysis of the data and can execute a data compression. The output of the data processing module 19 is supplied to the TCP/IP Ethernet connection 4.

The direction evaluation apparatus 11 includes a multiplier 20 which multiplies the first digital signal by a given factor. The direction evaluation apparatus 11 also includes a delay element 21 that introduces a given delay into the second digital signal, and an adder 22 by which the outputs of the delay element 21 and the multiplier 20 are added.

The down converter 12 executes, at least approximately, a Hilbert transform. For that purpose, the down converter 12 has a component 23 with an I/Q mixer and a subsequent component 24 having a Cartesian to polar converter. A portion of the component 23 having the I/Q mixer is provided with an NCO and an FIR filter, whereas the component 24 includes a FIR filter.

The signal processing unit 3 also includes a regulator unit 25 and a controller unit 26 for controlling the individual components of the signal processing unit 3. A transmitter control unit 27 is also provided. The regulator unit 25 analyses the first and second digital signals in response to a trigger signal received from the transmitter control element 27 and commands from the control unit 26 regarding multiplication factors for the multiplier 20, the delay for the delay element 21 and a switch setting that selects either automatic or manual control. The regulator unit 25 sets the multiplication factor for the multiplier 20, the delay for the delay element 21.

The control unit 26 sends to the transmitter control element 27 information about the transmission frequency produced by the transmitter, the signal return rate for the signal being emitted, so as to generate a sequence of signals to be transmitted. The control unit 26 also forwards a "burst-count" signal to the transmitter control element 27. The "burst-count" signal indicates how many bursts the EMAT produces in the ultrasound signal.

The transmitter control element 27 controls the unillustrated ultrasound transmitter. In particular, the transmitter control element 27 sets the time at which the ultrasound signal is transmitted, the frequency of the transmitted ultrasound signal and the return frequency of the ultrasound signals transmitted.

The control unit 26 controls the switches 15 and 17, which are optional elements that can vary the mode of the signal transmission. The switch 15 permits data to be output either as raw data or, data filtered by the median-filter. Through analysis of raw data compared to the data filtered by the median filter, the effectiveness of the median filter can, for example, be checked. The switch 17 provides a choice between linear data output and logarithmic data output. The control unit 26 also controls the filter in component 23 and the FIR filter in filter component 24 of the down-counter 12.

For non-destructive materials testing, a sequence of ultrasound signals is sent through a test object from an ultrasound transmitter (not shown). For example, the test object may, for example, be a belt moving underneath the ultrasound transmitter. Suitably, the ultrasound signals are transmitted across the direction traveled by the belt. The ultrasound receiver is suitably arranged in an area of the ultrasound transmitter and picks up the transmitted ultrasound signal and its reflections as its input signal. The transmission of the next ultrasound signal by the ultrasound transmitter begins when the signal is transmitted by the ultrasound transducer. The delay between the individual signal produced by the ultrasound transmitter is selected so that the excitation of the test object by a first ultrasound signal has completely died away before the next signal sequence is sent. This prevents the ultrasound receiver from picking up overlapping signals from the first and second ultrasound signals. When checking belts, 100 to 150 ultrasound signals are sent per second. Sending more ultrasound signals per second is, of course, also conceivable, depending on the shape of the test object. This is the case, especially when test objects are involved which quickly extinguish the test signal, or which severely dampen the signal.

Depending on the spatial arrangement of the first and second ultrasound transducers 1 and 2, the ultrasound signal is picked up, for example, first by the ultrasound transducer 2 and then by the ultrasound transducer 2, as the ultrasound signal passes by. The frequency of the ultrasound signal and the spatial arrangement of the ultrasound transducers 1, 2 are suited to one another so that distance between the ultrasound transducers 1 and 2 is a one-quarter wavelength delay ($\lambda/4$) of the ultrasound signal.

The ultrasound transducers 1, 2, preferably EMATs, convert the received ultrasound signal into a first analog signal HF0° and a second analog signal HF90°, and supply these two signals to the preamplifier 8. This preamplifier 8 is constructed as a constant, rather than a variable preamplifier, so as to amplify these signals using a constant amplification factor. The amplified signals are then supplied to the analog-to-digital converters 9, 10, which sample the analog signals at an 80 MHz sampling rate to produce two 14-bit digital signals.

The direction evaluation apparatus 11 delays the second digital signal by a delay of t/4. During subsequent addition of the processed signals, the signals are added constructively, when the ultrasound signal passes the ultrasound transducers 1, 2 in the predefined direction. The signals cancel each other out, when the ultrasound signals passes the ultrasound transducers 1, 2 from the opposite direction. The amplitude of the first digital signal can be adjusted by the multiplier 20 such that they are zeroed out, when the ultrasound signal passes the ultrasound transducers 1, 2, from the opposite direction.

The digital down converter 12 carries out a Hilbert transform. The summed digital signal input to the down-converter 12 is demodulated and processed by the FIR filter in filter component 24. The signal to be analyzed is then supplied by the down converter 12 to the converter 13 that changes the signal to a logarithmic signal so that the 24-bit signal is compressed into an 8-bit signal. The compressed 8-bit signal is supplied to the median-filter 14 and the switch 15. The median-filter 14, described in a more detailed manner below, produces an output signal that appears to be asynchronous with the return signal frequency, from "n" received input signals through the use of stochastic interference.

The subsequent switches 15, 17 enable the user to selectively output either raw data in linear or logarithmic form, or median-filtered data in linear or logarithmic form. Representation of this output is possible either on the local display screen 5 or by transmission through the Ethernet connection 4 for use by another computer.

Not only can the output signals be transmitted over the Ethernet connection 4, but, in addition, control data can also be inputted into the signal processing unit 3 over this connection. For example, remote fault analysis over the internet is possible. There is also the possibility that the test data can be sent over long distances.

Figure 2:
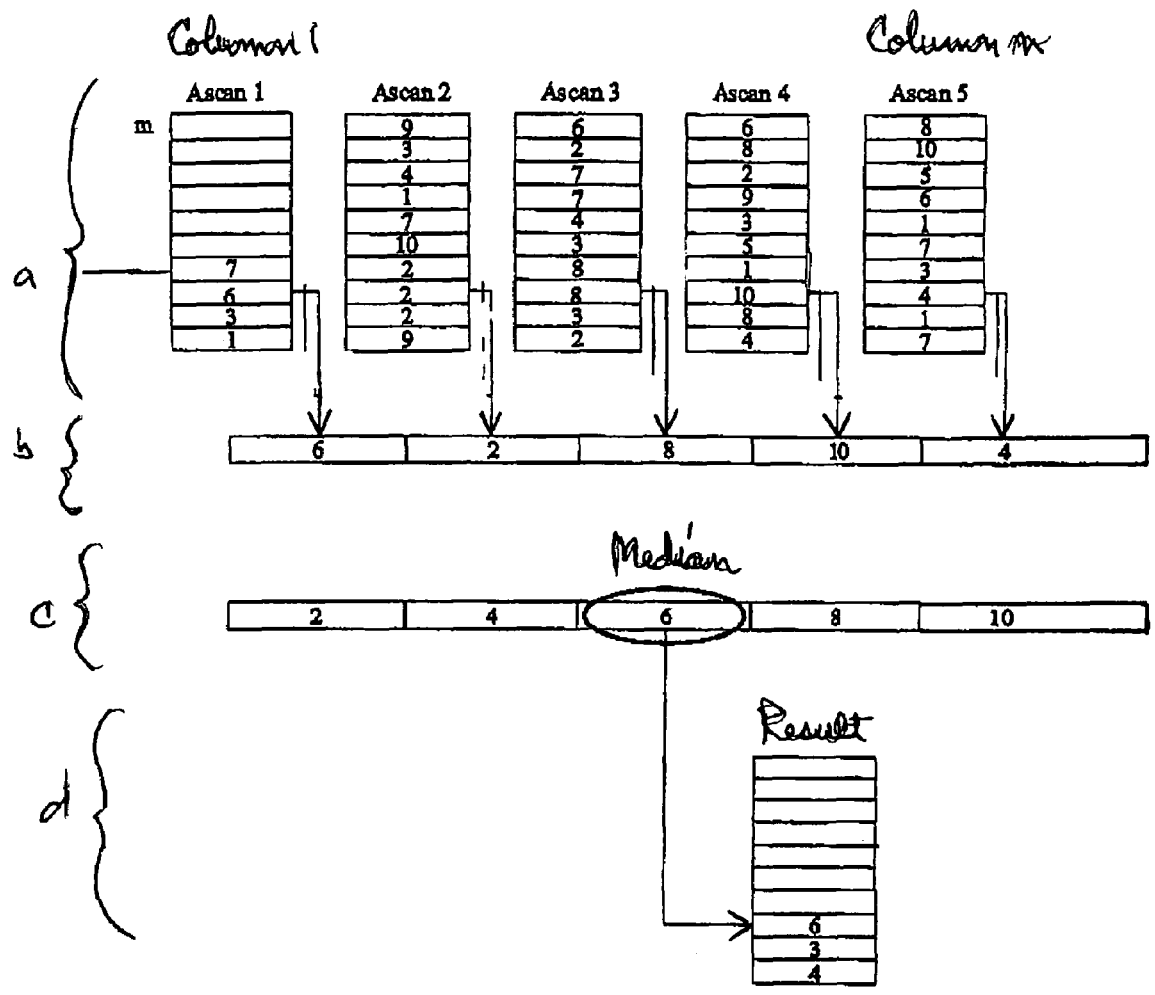
FIG. 2a-d show flowcharts of the operation of the median-filter of an ultrasound receiver in accordance with the present invention.

The mode of operation of the median filter will now be described in more detail, based on a median filter that determines a median value from five values, as shown in FIG. 2. Of course, the median-filter unit may determine a median value from other numbers of values, for example, three or seven.

The median-value filter 14 shown in FIG. 2 has five columns in the input matrix. Each column has "in" rows, wherein the number in corresponds to the number of samples of a signal. At the beginning of the measurement, all the columns have, preferably, the value 0. During evaluation of the first received ultrasound signal, the first column (Ascan1) is filled with values. When the evaluation of the first ultrasound signal is complete, the first column is full of values, and these values are all then shifted to the second column (Ascan2). At the beginning of the evaluation of the second ultrasound signal received, the first column fills with new values originating from the analysis of the second ultrasound signal. At the end of the analysis of the second ultrasound signal, the values in the second column (Ascan2) are all then shifted to the third column (Ascan3), whereas the values in the first column (Ascan1) are all shifted to the second column (Ascan2). The result of the analysis of the third ultrasound signal is recorded in the first column (Ascan1) values previously recorded in each column having been shifted to the next column as before. This shifting of values proceeds as an on-going, continuous process. Thus, at each time point, the results of the analysis of the next-to-last, third-last, fourth last, and fifth last ultrasound signals are found in their respective columns (Ascan 2-Ascan 5).

The first column (Ascan 1) of the input matrix (FIG. 2a) always contains the current actual sample values. The result array (FIG. 2d) contains the result of the median-filtering process. The result array has the same number of rows as each of the individual input columns in the input matrix. The value provided by each row in the result array is the result of median filtering each value in the corresponding row in each input column (Ascan1-Ascan5) in the input matrix. In FIG. 2b, a row selected from the input columns in the input matrix shows values stored in a corresponding place in each of the individual input arrays. These values, shown in FIG. 2b, are rearranged in ascending order to show in FIG. 2c that "6" is the median value in row. The result array is then filled with each of the median values thus determined for each subsequent sampling time. By using a shortened shifting process that fills only the first three columns in the input matrix, a median-filtered output can be produced in real time.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

What is claimed is:

1. A signal processing apparatus for an ultrasound transducer, comprising:
   a first preamplifier for amplifying an analog signal produced by an ultrasound transducer to generate an amplified analog signal;
   a first analog-to-digital converter directly connected to the preamplifier for producing a sequence of first digital signals from the amplified analog signal; and
   a median filter for filtering the sequence of first digital signals, each of said first digital signals having a respective row of values in which each subsequent value in the row represents the value of the signal at the next sampling point of m sampling points that are recorded in a sampling window for each first digital signal, said first analog-to-digital converter being connected to a first median filter for filtering the sequence of first digital signals recorded in n sampling windows to produce a sequence of first filtered digital signals, said median filter being adapted to transfer a sequence of n rows having m values in each row to respective columns in an input matrix, sort the values in each row of the input matrix by size and output the value in each respective row that has the median size in the respective row of the input matrix to a result array, the values output to the result array providing a first median digital signal used to produce an output signal for the ultrasound transducer.

2. The signal processing apparatus of claim 1, further comprising a demodulator for producing a sequence of demodulated digital signals from the sequence of first digital signals.

3. The signal processing apparatus of claim 1, wherein the analog-to-digital converter has at least a 14-bit resolution and at least a 50 MHz clock frequency.

4. The signal processing apparatus of claim 2, wherein the demodulator carries out a Hilbert transformation of the sequence of first digital signals.

5. The signal processing apparatus of claim 2, wherein the demodulator has an NOC, an I/Q mixer and CIC filter, and an FIR filter and Cartesian-to-polar coordinate converter.

6. The signal processing apparatus of claim 1, wherein the preamplifier is a constant preamplifier.

7. The signal processing apparatus of claim 1, further comprising a switch-controlled bypass for the median filter.

8. The signal processing apparatus of claim 1, further comprising an Ethernet connection for connecting digital signals in the ultrasound receiver to a network.

9. The signal processing apparatus of claim 1, further comprising a second ultrasound transducer generating a second analog signal; a second preamplifier amplifying the second analog signal to produce an amplified analog signal; and a second analog-to-digital converter directly connected to the second preamplifier for producing a second digital signal from the amplified analog signal produced by the second preamplifier.

10. The signal processing apparatus of claim 9, further comprising a multiplier for adjusting the first digital signal to produce a multiplied signal; a delay element for adjusting the second digital signal to produce a delayed signal; and an adder for adding the multiplied signal and the delayed signal to produce an addition signal.

11. The signal processing apparatus of claim 10, wherein the multiplier has an adjustable multiplication factor.

12. The signal processing apparatus of claim 10, wherein the delay element has an adjustable delay.

13. The signal processing apparatus of claim 10, further comprising an analyzer for observing the first and the second digital signal.

14. The signal processing apparatus of claim 10, wherein the multiplier has an adjustable multiplication factor, further comprising an analyzer for observing the first and the second digital signal, which analyzer determines the multiplication factor.

15. The signal processing apparatus of claim 10, wherein the multiplier has an adjustable multiplication factor, further comprising an analyzer for observing the first and the second digital signal, which analyzer controls the multiplication factor.

16. The signal processing apparatus of claim 10, wherein the delay has an adjustable delay further comprising an analyzer for observing the first and the second digital signal, which analyzer determines the delay.

17. The signal processing apparatus of claim 10, wherein the delay has an adjustable delay, further comprising an analyzer for observing the first and the second digital signal, which analyzer controls the delay.

18. The signal processing apparatus of claim 10, further comprising means for manually controlling at least one of said adjustments to the first and second digital signals for observing the addition signal.

19. The signal processing apparatus of claim 18, wherein at least one of said adjustments to the first and second digital signals has a predetermined value.

20. The signal processing apparatus of claim 1, wherein a 400 µs window is used to provide 32,000 sampling points when signals sent at 6 millisecond intervals.

21. A signal processing apparatus for an ultrasound transducer, comprising:
  a first analog-to-digital converter directly connected to the ultrasound transducer for producing a sequence of first digital signals from a sequence of first analog signals produced by the ultrasound transducer; and
  a demodulator for producing a sequence of demodulated digital signals from the sequence of first digital signals, said demodulator being spatially separated from said first analog-to-digital converter, wherein the demodulator includes an NOC, an I/Q mixer and CIC filter, and an FIR filter and a Cartesian-to-polar coordinate converter.

22. The signal processing apparatus of claim 21, wherein the demodulator carries out a Hilbert transformation of the sequence of first digital signals.

23. The signal processing apparatus of claim 21, further comprising a median filter for filtering a sequence of the digital signals to produce a filtered digital signal.

24. The signal processing apparatus of claim 23, further comprising a switch-controlled bypass for the median filter.

25. The signal processing apparatus of claim 21, further comprising an Ethernet connection for connecting digital signals in the ultrasound receiver to a network.

26. The signal processing apparatus of claim 21, further comprising a second analog-to-digital converter producing a second digital signal from an analog signal produced by a second ultrasound transducer.

27. A signal processing method, comprising the steps of:
  producing a sequence of analog signals from an ultrasound transducer;
  amplifying in the sequence of analog signals in a preamplifier to a sequence of amplified analog signals;
  providing the sequence of amplified analog signals to an analog-to-digital converter directly connected to the preamplifier to produce a sequence of first digital signals from the sequence of amplified analog signals wherein each of said first digital signals in the sequence of first digital signals has a respective row of values in which each subsequent value in the row represents the value of the respective first digital signal at the next sampling point of m sampling points that are recorded in a sampling window,
  providing the rows of values for the sequence of first digital signals to a median filter for filtering the sequence of first digital signals recorded in n sampling windows to produce a sequence of first filtered digital signals;
  transferring a sequence of n rows having m values in each row to an respective columns in an input matrix;
  sorting the values in each row of the input matrix by size;
  providing the value that has the median size in each row of the input matrix to a result array; and
  using the values in the result array to produce a first output digital signal for the ultrasound transducer.

28. The signal processing method of claim 27, further comprising the step of supplying the sequence of first digital signals to a demodulator to produce a sequence of first demodulated digital signals.

29. The signal processing method of claim 27, wherein the preamplifier is a constant preamplifier.

30. The signal processing method of claim 27, wherein a 400 µs window is used to provide 32,000 sampling points when signals sent at 6 millisecond intervals.

* * * * *